US010107786B2

(12) United States Patent
Fan

(10) Patent No.: US 10,107,786 B2
(45) Date of Patent: Oct. 23, 2018

(54) ULTRASONIC FLOW METER CLAMP

(71) Applicants: GENERAL ELECTRIC COMPANY, Schenectady, NY (US); Kai Fan, Shanghai (CN)

(72) Inventor: Kai Fan, Shanghai (CN)

(73) Assignee: General Electric Company, Schenectady, NY (US)

( * ) Notice: Subject to any disclaimer, the term of this patent is extended or adjusted under 35 U.S.C. 154(b) by 99 days.

(21) Appl. No.: 15/115,602

(22) PCT Filed: Feb. 4, 2014

(86) PCT No.: PCT/CN2014/071862

§ 371 (c)(1),
(2) Date: Jul. 29, 2016

(87) PCT Pub. No.: WO2015/117263

PCT Pub. Date: Aug. 13, 2015

(65) Prior Publication Data

US 2017/0160240 A1 Jun. 8, 2017

(51) Int. Cl.
*G01N 29/28* (2006.01)
*G01F 15/18* (2006.01)
*G01F 1/66* (2006.01)

(52) U.S. Cl.
CPC ............. *G01N 29/28* (2013.01); *G01F 1/667* (2013.01); *G01F 15/18* (2013.01); *G01N 2291/101* (2013.01)

(58) Field of Classification Search
CPC .. G01N 29/28; G01N 2291/101; G01F 15/18; G01F 1/667

(Continued)

(56) References Cited

U.S. PATENT DOCUMENTS 4,286,470 A 9/1981 Lynnworth
4,373,401 A * 2/1983 Baumoel ................ G01F 1/662 310/327

(Continued)

FOREIGN PATENT DOCUMENTS

| | | | |
|---|---|---|---|
| CN | 102359802 | A | 2/2012 |
| CN | 202748065 | U | 2/2013 |
| JP | 2013174567 | A | 9/2013 |

OTHER PUBLICATIONS

International Search Report and Written Opinion issued in connection with corresponding Application No. PCT/CN2014/071862 dated Nov. 15, 2014.

*Primary Examiner* — J M Saint Surin
(74) *Attorney, Agent, or Firm* — Mintz Levin Cohn Ferris Glovsky and Popeo, P.C.

(57) ABSTRACT

A clamping apparatus for coupling an ultrasonic transducer to a conduit is disclosed. The clamping apparatus comprises a base portion fastened to the conduit and including a bracket for receiving an adapter. The adapter is attached to a housing and allows the housing to be rotated when the adapter is positioned in an upper portion of the bracket, and prevents the housing from being rotated when the adapter is positioned in a lower portion of the bracket. The housing is configured to enclose the ultrasonic transducer except for a housing opening along the bottom of the housing. The ultrasonic transducer extends through the housing opening and is spring biased against the conduit.

20 Claims, 6 Drawing Sheets

100
107 109 111 150 111 113 101
103
113 105 104 108 104 105

(58) Field of Classification Search
USPC .......................................................... 73/649
See application file for complete search history.

(56) References Cited

U.S. PATENT DOCUMENTS

| | | | | |
|---|---|---|---|---|
| 4,425,803 | A * | 1/1984 | Baumoel | G01F 1/667 73/861.18 |
| 6,349,599 | B1 * | 2/2002 | Lynnworth | G01N 29/223 73/644 |
| 6,397,683 | B1 * | 6/2002 | Hagenmeyer | G01F 1/662 73/861.18 |
| 7,469,599 | B2 * | 12/2008 | Froehlich | G01F 1/66 73/861.27 |
| 7,669,483 | B1 * | 3/2010 | Feller | G01F 1/662 24/279 |
| 8,714,030 | B1 * | 5/2014 | Liu | G01F 1/662 73/861.28 |
| 9,134,157 | B2 * | 9/2015 | van Klooster | G01F 1/662 |
| 2002/0108450 | A1 * | 8/2002 | Ohnishi | G01F 1/662 73/861.27 |
| 2003/0041674 | A1 | 3/2003 | Ohnishi | |
| 2003/0172743 | A1 * | 9/2003 | Ao | G01F 1/662 73/861.27 |
| 2007/0232919 | A1 | 10/2007 | Pors et al. | |
| 2008/0022776 | A1 | 1/2008 | Buchanan | |
| 2008/0232919 | A1 * | 9/2008 | Anderson | B60P 3/077 410/30 |
| 2011/0120231 | A1 | 5/2011 | Berger et al. | |

* cited by examiner

ULTRASONIC FLOW METER CLAMP

BACKGROUND

The subject matter disclosed herein relates to ultrasonic flow meters for measuring a volume of fluid flowing through a conduit, such as a pipe. In particular, it is directed to a clamping apparatus for coupling ultrasonic transducers to the conduit.

Mechanisms for connecting ultrasonic transducers to fluid carrying conduits must secure the ultrasonic transducers against the conduit with sufficient pressure so that the ultrasonic transducers are acoustically coupled to the conduit walls and the fluid flowing therein. Ultrasonic signals traveling between the ultrasonic transducers must traverse a solid or liquid acoustic path to ensure accurate signal measurements. Known mechanisms used to couple ultrasonic transducers to conduits comprise clamps having large, complex frames surrounding the conduit to secure the ultrasonic transducers. Maintenance and adjustment of such ultrasonic transducer assemblies requires a technician to disassemble and reassemble several parts of the assembly using specialized tools.

The discussion above is merely provided for general background information and is not intended to be used as an aid in determining the scope of the claimed subject matter.

BRIEF DESCRIPTION

A clamping apparatus acoustically couples an ultrasonic transducer to a conduit. A base portion of the apparatus is fastened to the conduit and includes brackets for receiving an adapter. The adapter is attached to a housing and allows the housing to be rotated when the adapter is positioned in an upper portion of the brackets, and prevents the housing from being rotated when the adapter is positioned in a lower portion of the brackets. The housing is configured to enclose the ultrasonic transducer except for a housing opening along the bottom of the housing where the ultrasonic transducer transmits and receives ultrasonic signals. The ultrasonic transducer extends through the housing opening and is spring biased against the conduit. It may be realized in the practice of some disclosed embodiments of the clamping apparatus disclosed herein that the embodiments provide convenient, simple installation and maintenance of an ultrasonic transducer for measuring fluid flow in a conduit.

This brief description is intended only to provide a brief overview of subject matter disclosed herein according to one or more illustrative embodiments, and does not serve as a guide to interpreting the claims or to define or limit the scope of the application, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features disclosed herein can be understood, a detailed description may be had by reference to certain embodiments, some of which are illustrated in the accompanying drawings. It is to be noted, however, that the drawings illustrate only certain embodiments and are therefore not to be considered limiting of its scope, for the scope of the application encompasses other equally effective embodiments. The drawings are not necessarily to scale, emphasis generally being placed upon illustrating the features of certain embodiments. In the drawings, like numerals are used to indicate like parts throughout the various views. Thus, for further understanding of the embodiments, reference can be made to the following detailed description, read in connection with the drawings in which.

DETAILED DESCRIPTION

Figure 1:
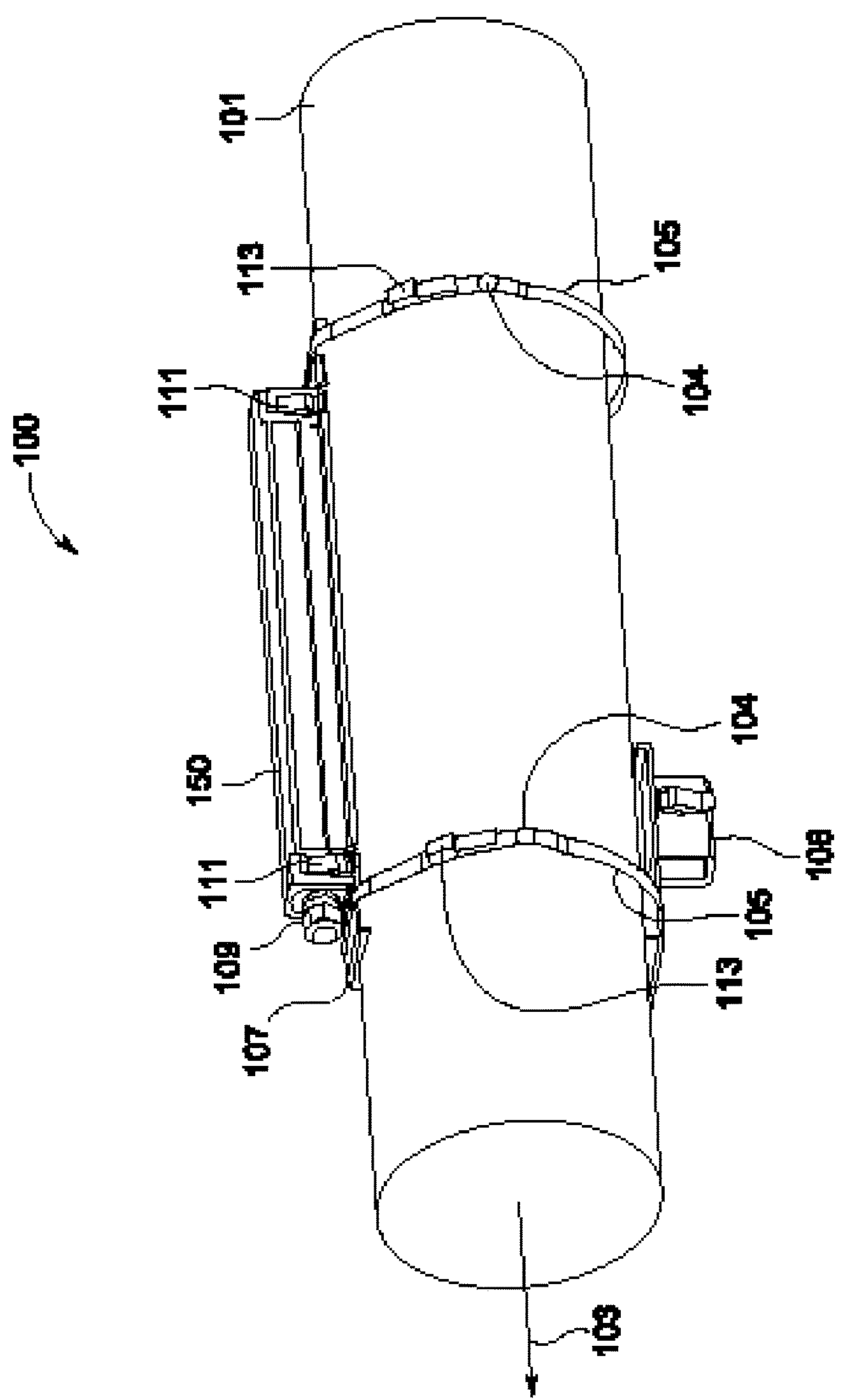
FIG. 1 is a perspective view of an ultrasonic clamping apparatus fastened to a conduit.
Figure 2:
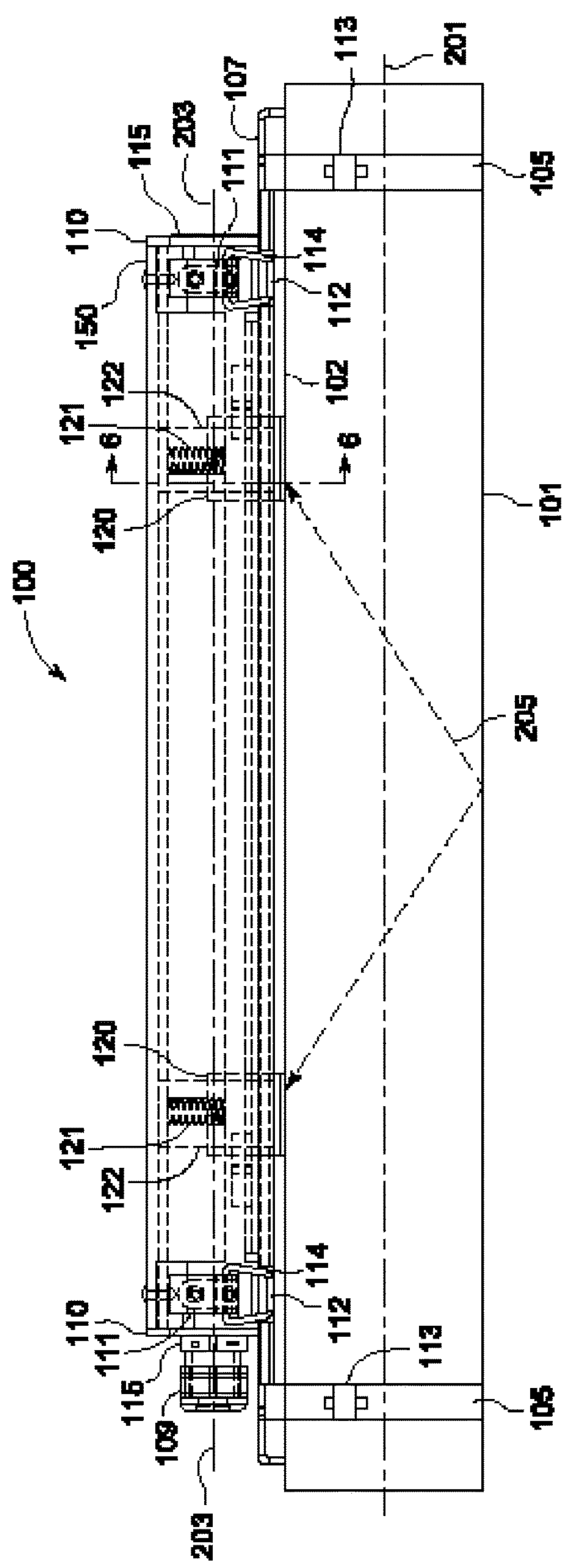
FIG. 2 is a side view of the ultrasonic clamping apparatus of FIG. 1.

With reference to FIGS. 1 and 2, an ultrasonic clamping apparatus 100 for coupling ultrasonic transducers 120 to a conduit 101 is illustrated. The conduit 101 may be used to deliver gases, liquids or other fluids in the direction indicated by the arrow 103, for example, and the ultrasonic transducers 120 may be used to measure a flow rate of the fluid and, thereby, the volume of the fluid so delivered. Fastened to one side of the conduit 101 the ultrasonic clamping apparatus 100 secures a pair of ultrasonic transducers 120 within the ultrasonic transducer housing 150 and against the conduit 101. The ultrasonic clamping apparatus 100 further includes a base plate 107 that is fastened to the conduit 101 using straps 105 wrapped around the outside surface (circumference) of the conduit 101 and over each of two ends of the base plate 107. The straps 105 serve to secure the base plate 107 tightly against the outside surface of the conduit 101 and maintain the base plate 107 in a substantially fixed position thereon.

The straps 105 are made from a material that is strong enough to secure the base plate 107 to the conduit 101 without excessive stretching (loosening) of the straps 105 over time, such as stainless steel straps. The straps 105 may also be of the type that is tightened against the conduit by manually pulling the strap through a loop and securing the strap using a clamp 113, or they may be of the type that is tightened by turning a screw that engages slots in at least one end portion of the strap 105 where it overlaps its other end. To further ensure a tight fit of the straps 105 against the outside surface of the conduit 101, spring washers 104 may be placed underneath the straps 105 such as between the straps 105 and the conduit 101. The spring washers 104 are spring biased to expand so that the straps 105 are further tightened against the base plate 107. The spring washers 104 may also be placed directly underneath the straps 105 such as between the straps 105 and the base plate 107 where the straps 105 cross over the ends of the base plate 107. The straps 105 may also include visible measurement markings thereon for measuring and manually positioning additional fixtures on the conduit 101, such as fixture 106 on a bottom side of the conduit 101 opposite the ultrasonic transducers 120. The fixture 106 may include another ultrasonic transducer configured to communicate with the ultrasonic transducers 120 within the clamping apparatus 100. The measurement markings on the straps 105 may comprise ruled markings with corresponding numbers indicating a distance measured in inches, for example. The markings may be ink based markings or they may be mechanically inscribed, punched, or otherwise formed on the straps 105. The ultrasonic transducer housing 150 is attached to the base plate 107 using latches 111 affixed to each side and to each end of the ultrasonic transducer housing 150, as will be explained below.

A communication cable (not shown) may be electronically coupled to each of the ultrasonic transducers 120 within the housing 150 by introducing the cable into an interior region of the housing 150 through a cable gland 109 attached to one end of the housing 150. The communication cable may be connected to each of the ultrasonic transducers 120 via the cable connectors 123 (FIG. 3) which are each electrically connected to one of the ultrasonic transducers 120. The communication cable allows a computer processing system to electronically communicate with, and control operation of, the ultrasonic transducers 120 for calculating the flow rate of fluid traveling through the conduit 101, as is well known. The processing system may be programmed to cause a first one of the ultrasonic transducers 120 to emit a pattern of ultrasonic signals through the wall of the conduit 101, into the fluid traveling therethrough, and to detect echoes of the emitted ultrasonic signals, as they reflect off of the opposing interior wall of the conduit 101, at the second one of the ultrasonic transducers 120. The time-of-flight, or delay time, of the ultrasonic signals, as measured by the processing system, enables the processing system to calculate the flow rate of the fluid traveling through the conduit 101.

Referring in particular to FIG. 2, there is illustrated a side view of the ultrasonic clamping apparatus 100 attached to the conduit 101, wherein the ultrasonic transducer housing 150 is shown in a transparent view to illustrate the positions of the ultrasonic transducers 120 within the housing 150. The ultrasonic transducers 120 are secured within ultrasonic transducer frames 122 which also contain a spring 121 for pressing the ultrasonic transducers 120 against the outside surface of the conduit 101 to ensure that the ultrasonic transducers 120 are securely acoustically coupled to the conduit 101. The housing 150 includes a bottom opening 153 (FIG. 3) aligned with an opening in the base plate 107 which allows the transducers 120 to extend therethrough and make contact with the conduit 101. The springs 121 are each attached to an interior surface of the ultrasonic transducer frame 122 and to the top of the ultrasonic transducer 120. The ultrasonic transducers 120, in turn, extend through an opening in the bottom of the ultrasonic transducer housing 150 and in the top of the base plate 107 and are pressed by the springs 121 against the outside surface of the conduit 101. The housing 150 is substantially elongated in shape and so comprises a longitudinal axis 203 that is substantially aligned in parallel with a central axis 201 of the conduit 101.

As shown in FIG. 2, the base plate 107 includes first and second brackets 110 proximate opposite ends of the base plate 107 that extend vertically from, i.e., perpendicular to, the longitudinal axis 203. The first and second brackets 110 may be integrally formed with the base plate 107 perpendicular thereto. The ultrasonic transducer housing 150, attached to the base plate 107 using clamps 111, maintains the ultrasonic transducers 120 in physical contact with, i.e., acoustically coupled to, the outside surface of the conduit 101. The housing 150 surrounds the ultrasonic transducers 120 and comprises a lengthwise opening 153 along its bottom side that faces the conduit 107 when the housing 150 is rotated into a vertical operative position. In operation, an ultrasonic signal transmitted by one of the ultrasonic transducers 120 travels through a wall of the conduit 101 into the fluid traveling through the conduit 101 and reflects off of the opposite wall of the conduit 101 to the other ultrasonic transducer 120, as illustrated by the ultrasonic signal path 205.

The latches 111 are each attached to the housing 150 on opposite sides and proximate opposite ends of the housing 150. The latches 111 each comprise a loop 114 that engages a base plate lip 112 to secure the housing 150 against the base plate 107 when the latches are manually closed. When the latches 111 are manually released (opened), the force of the springs 121 causes the housing 150 to be lifted upward, as will be explained below, whereby the housing 150 may be rotated to access the ultrasonic transducers 120 through the bottom opening 153 of the housing 150 for maintenance, modification, repair, or other adjustments.

Figure 3:
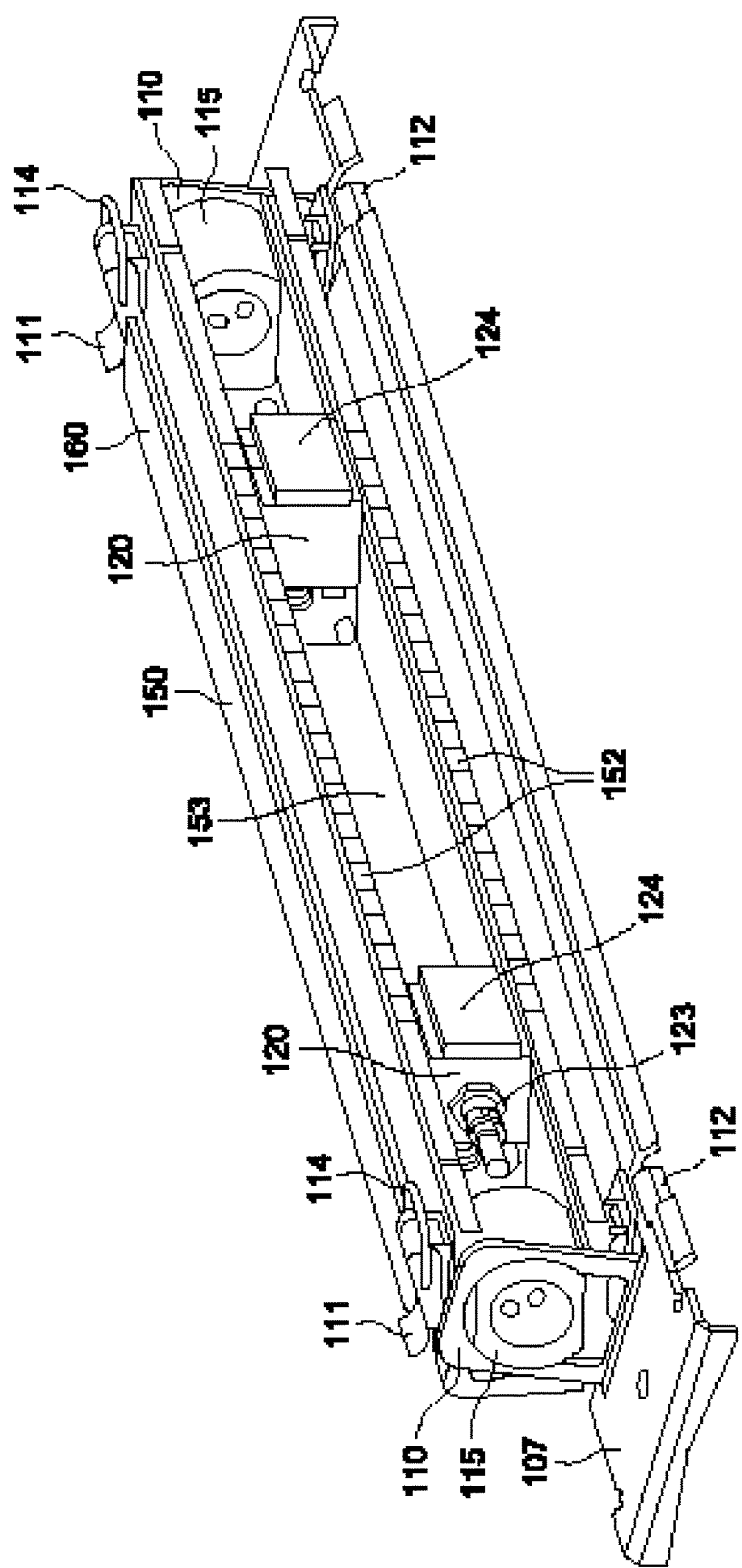
FIG. 3 is a perspective view of the ultrasonic clamping apparatus of FIG. 1 with the conduit removed and after rotating the ultrasonic transducer housing.

Referring to FIG. 3, wherein the conduit 101, the straps 105, and the cable gland 109 have been removed for ease of illustration, the housing 150 comprises parallel rails 152 on two opposing sides of the longitudinal opening 153 in the bottom of the housing 150 which support the ultrasonic transducer frames 122 and secure the ultrasonic transducers 120 in a fixed position against an outside surface of the conduit 101 when the latches 111 are closed. The rails 152 are configured to allow the transducer frames 122 to slide along the rails 152 when the latches 111 are released (opened). In the opened position, the springs 121 lift the ultrasonic transducer housing 150 which also reduces their pressure against the ultrasonic transducers 120 causing the ultrasonic transducers 120 to loosely contact the conduit 101. In this loosened position, the ultrasonic transducers 120 may be moved closer together or further apart by sliding them along the rails 152 of the housing 150, and the housing 150 may be rotated to the sideways position shown in FIG. 3 so that access to the ultrasonic transducers 120 may be easily provided.

The housing 150 includes an adapter 115 on each end for securing the housing 150 to the brackets 110 of the base plate 107 and to permit the housing 150 to be rotated into the access position shown in FIG. 3 where the two ultrasonic transducers 120 are visible through the opening 153 in the bottom of the housing 150. The rails 152 adjacent the opening 153 in the bottom of the housing 150 may be marked by ruled lines so that the distance between the ultrasonic transducers 120 can be easily visually determined while their position is manually adjusted by sliding them along the rails 152. In an alternative arrangement, one of the ultrasonic transducers 120 may be permanently fixed in position while only the other ultrasonic transducer 120 is movable along the rails 152.

The housing 150 of the ultrasonic clamping apparatus 100 may be rotated from the access position shown in FIG. 3 to an operative position, e.g., FIG. 2, so that the ultrasonic transducers 120 face downward toward the conduit 101. The latches 111 may then be manually engaged to their corresponding base plate lip 112 to close the latches 111 and press the ultrasonic transducers 120 against the outside surface of the conduit 101. In the closed position, the ultrasonic transducers 120 may be activated to perform fluid flow measurements as described herein. The cable gland 109 may include a threaded outside surface to engage threads on the interior surface of the adapter 115 for attaching the cable gland 109 thereto.

As shown in FIG. 3, the opening 153 in the bottom of the housing 150 is a longitudinal opening extending from one end of the housing 150 to the other. Proximate the two opposing ends of the housing 150, the opening 153 widens so that when the ultrasonic transducers 120 are moved toward either of these opposing ends they may be disengaged from the rails 152 and removed from inside the housing 150 through the wider portion of the opening 153. This makes for convenient replacement, maintenance, or repair of the ultrasonic transducers 120.

Figure 4:
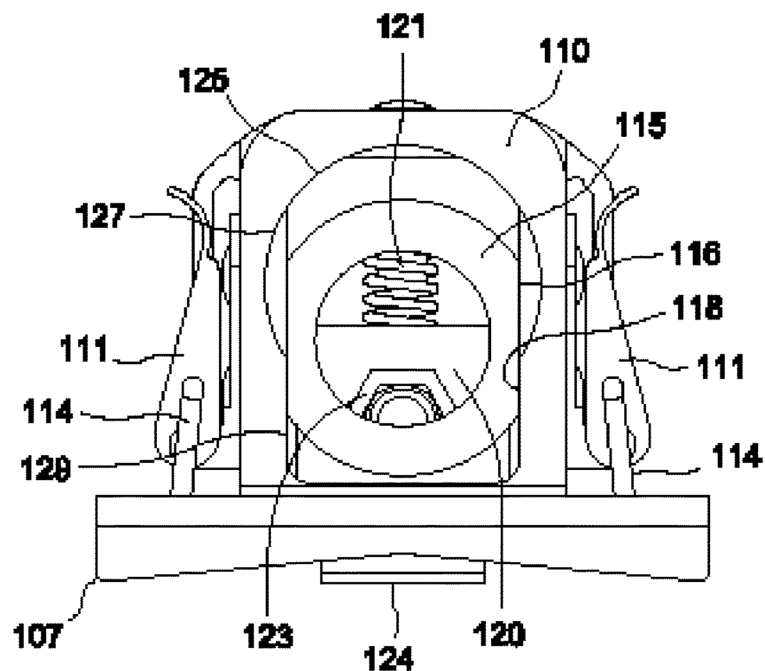
FIG. 4 is an end view of the ultrasonic clamping apparatus with the cable gland removed.
Figure 5:
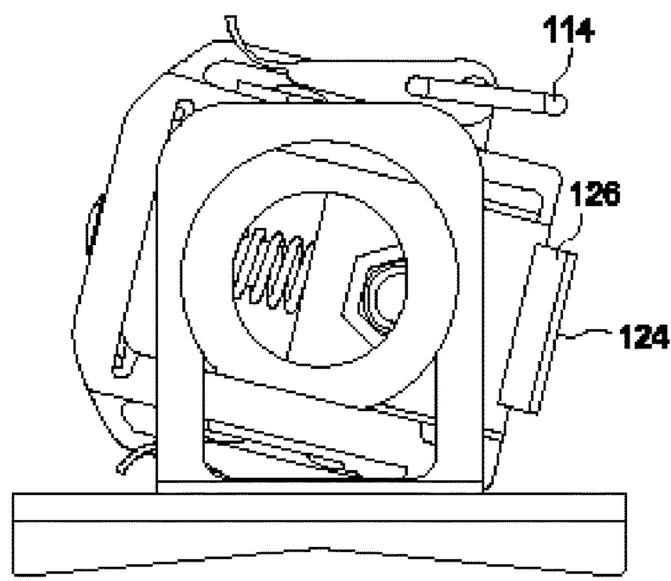
FIG. 5 is an end view of the ultrasonic clamping apparatus of FIG. 4 after rotating the ultrasonic transducer housing.

Referring to FIGS. 4 and 5 there is illustrated an end view of the portion of the ultrasonic clamping apparatus 100 as shown in FIG. 3, wherein the closed operative position of the ultrasonic clamping apparatus 100 is shown in FIG. 4 and the opened access position of the ultrasonic clamping apparatus 100 is shown in FIG. 5. As illustrated in these figures, an opening 125 in the bracket 110 comprises two portions. The upper portion 127 of the opening 125 is substantially circular and has a diameter slightly larger than a diameter of the adapter 115 so that the adapter 115 and housing 150 may be freely rotated when the adapter 115 is positioned therein (the opened position), as shown in FIG. 5. The adapter 115 may be positioned in the lower portion 129 of the opening 125 by aligning the edges 116 of the adapter 115 with the edges 118 of the lower portion of the opening 129 and sliding the adapter 115 into the lower portion 129 (the closed position) and manually closing the latches 111, as shown in FIG. 4. Because the linear edge 116 of the adapter 115 engages the linear edge 118 of the lower portion 129 of the opening 125, the adapter 115 and housing 150 cannot be rotated. In this closed position, the ultrasonic transducers 120 extend through the bottom opening 153 of the housing 150 and through an opening in the top of the base plate 107 to make contact with, and become acoustically coupled, to the outside surface of the conduit 101. The springs 121 cause the ultrasonic transducers 120 to be pressed against the outside surface of the conduit 101 and ensure acoustic coupling therebetween. The adapter 115 may be fixedly attached to the housing 150 at opposing inside surfaces of the housing 150 so that the adapter 115 and the housing 150 rotate together when the housing 150 is manually grasped to position the adapter 115 in the upper portion 127 of the opening 125 and rotated, or when the adapter 115 is moved into the lower portion 129 of the opening 125 for securing the ultrasonic transducers 120 against the outside surface of the conduit 101.

Figure 6:
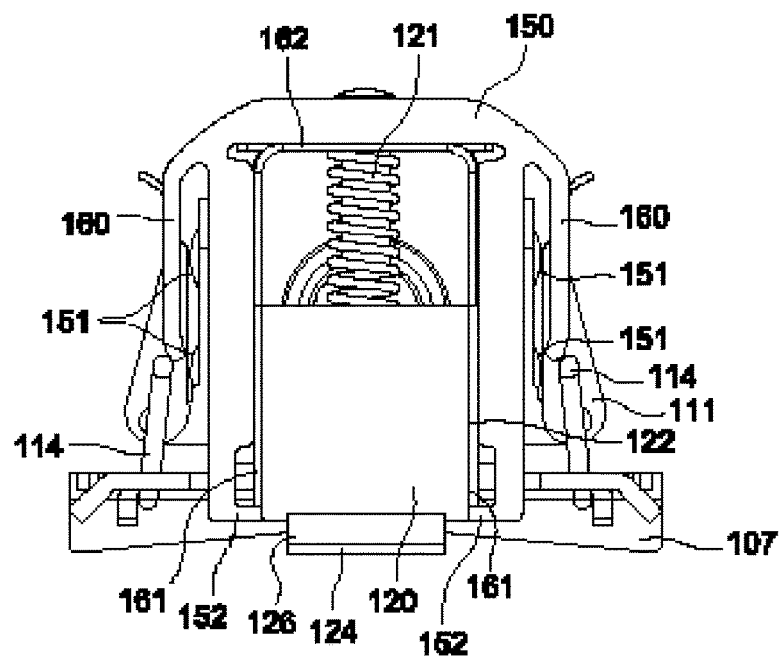
FIG. 6 is a cross-sectional end view of the ultrasonic clamping apparatus of FIG. 4.

With reference to FIG. 6, there is shown a cross-section end view through the housing 150, base plate 107, and ultrasonic transducer 120 of the ultrasonic clamping apparatus 100. As shown in the figure, the ultrasonic transducer 120 is disposed within an ultrasonic transducer frame 161 that abuts the ultrasonic transducer 120 on opposite sides thereof and encloses the spring 121 that applies a force against an inside surface of the ultrasonic transducer frame 161 and against the top of the ultrasonic transducer 120. The ultrasonic transducer frame 161 further abuts inside walls of the housing 150 on three sides, and contacts the rails 152 along which the ultrasonic transducer frame 161 slides to manually move the ultrasonic transducer 120 into a desired position within the housing 150. The ultrasonic transducers 120 include an acoustic coupling plate 126 and a coupling layer 124. The coupling layer 124 may comprise a suitable coupling material, such as Teflon tape, grease, a gel, or other viscous material, applied to a surface of the coupling plate 126 that faces the conduit 101 to enable acoustic coupling as between the coupling plate 126 and the conduit 101 (FIG. 1). The latches 111 on either side of the housing 150 are affixed thereto using, for example, rivets 151. When the latches 111 are closed, the action of the housing 150 against the spring 121 presses the ultrasonic transducer 120 against the outside surface of the conduit 101. The compressed spring 121 thereby maintains acoustic coupling as between the coupling plate 126, coupling layer 124, and the outside surface of the conduit 101. When the latches 111 are released, or opened, the spring 121 inside the ultrasonic transducer frame 161 lifts the housing 150 until a bottom edge of the housing 150 clears the top of the base plate 107 which enables the housing 150 to be rotated (FIG. 3), thereby exposing the ultrasonic transducers 120 through the opening 153 in the bottom of the housing 150 and providing convenient access to the ultrasonic transducers 120.

The housing 150 may include overhangs 160 on opposite sides of the housing 150 which extend from the top of the housing 150 downward substantially parallel and spaced apart from the exterior walls of the housing 150 leaving a gap between the overhangs 160 and the walls of the housing 150. Any wires that may be required to extend exterior to and along the housing 150 may be inserted, or tucked, into the gap to prevent exposure and/or entanglement thereof. These wires may include communication lines connected to a processing system and to the ultrasonic transducers 120 for controlling ultrasonic signaling thereof.

Figure 7:
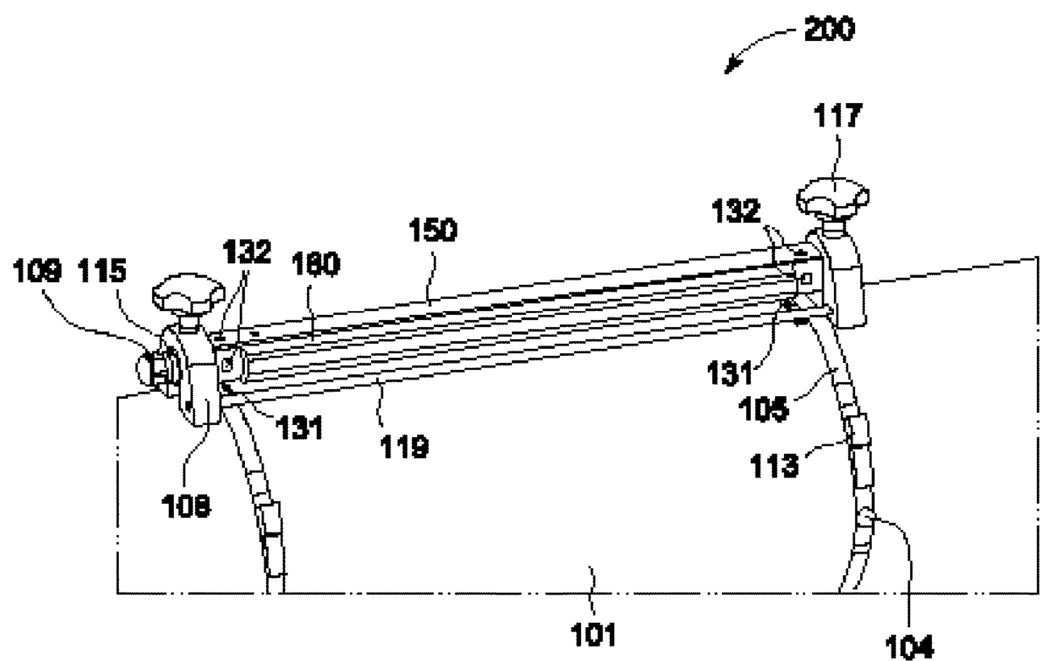
FIG. 7 is a perspective view of a second embodiment of an ultrasonic clamping apparatus fastened to a conduit.
Figure 8:
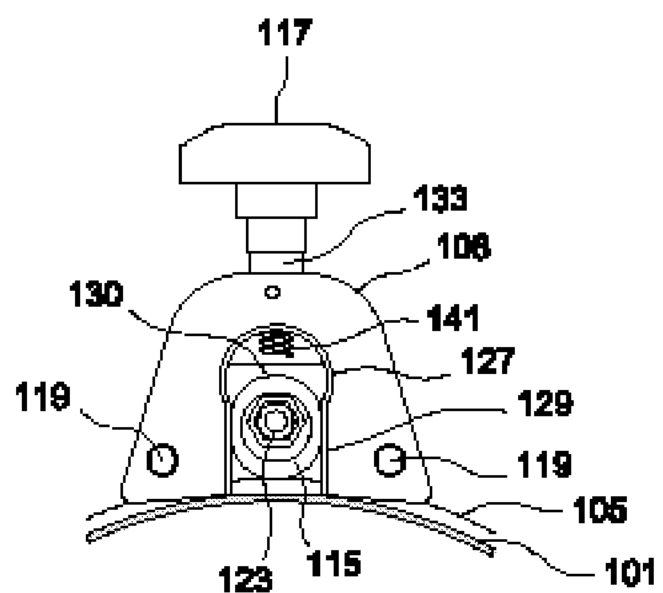
FIG. 8 is an end view of the ultrasonic clamping apparatus of FIG. 7 with the cable gland removed.

With reference to FIGS. 7 and 8, another embodiment of an ultrasonic clamping apparatus 200 for coupling ultrasonic transducers 120 to a conduit 101 is illustrated. Like numerals are used to indicate like parts which comprise features identical to those described above and illustrated in the various figures. The ultrasonic clamping apparatus 200 is fastened to one side of the conduit 101 using straps 105 that secure base plates 131 to the conduit 101. The straps 105 are wrapped around the outside surface (circumference) of the conduit 101 and over each of two base plates 131. The straps 105 serve to secure the base plates 131 tightly against the outside surface of the conduit 101 and maintain the base plates 131 in a substantially fixed position thereon.

The ultrasonic transducer housing 150 is attached to the adapters 115 using rivets or screws 132. First and second base plates 131 include first and second brackets 108 attached thereto that extend vertically from, i.e., perpendicular to, the longitudinal axis 203 of the housing. The first and second brackets 108 may be integrally formed with the base plates 131 and perpendicular thereto. The ultrasonic transducer housing 150, attached to the adapters 115 secures and maintains the ultrasonic transducers 120 in physical contact with, i.e., acoustically coupled to, the outside surface of the conduit 101.

In the embodiment illustrated in FIGS. 7 and 8, the latches 111 described above are not used. Instead, the base plate 107 is replaced with two separate base plates 131 having their brackets 108 joined together by stabilizer bars 119 on either side of the housing 150. The straps 105 cross over the base plates 131 on an inward side of the brackets 108 rather than the outward side as illustrated in, for example, FIG. 1.

Referring in particular to FIG. 8, the brackets 108 each include a hand wheel 117 for pressing the spring 141 against a top surface 130 of the adapter 115. The springs 141 replace the springs 121 in the embodiments of FIGS. 1-6. Using the springs 141 to bias the adapters 115 and the housing 150, attached thereto, toward the outside surface of the conduit 101, the ultrasonic transducers 120, secured in the housing 150, are pressed against the outside surface of the conduit 101 to establish acoustic coupling therewith. The hand wheels 117 each include a shaft 133 that is threaded at one end and that engages threaded openings (not shown) in the brackets 108 for rotating the hand wheels and moving the shaft 133 toward the conduit 101. Attached to an end of the shaft 133 is the spring 141 which may be compressed against the adapter 115 when the hand wheel 117 is rotated to a closed position. When the hand wheel 117 is rotated to an open position, the spring may be disengaged from the top surface 130 of the adapter 115 (shown in FIG. 8) which loosens the adapter 115 and the housing 150, attached thereto. This allows the adapter 115 to be placed into the upper portion 127 of the bracket opening 125 and rotated for accessing the ultrasonic transducers 120, as explained herein, to access the ultrasonic transducers 120 through the bottom opening 153 of the housing 150 for maintenance, modification, repair, or other adjustments. Thus, in the embodiment illustrated in FIGS. 7 and 8, when the housing 150 is rotated to be moved into a closed position, instead of securing latches 111 as described above in relation to the embodiments of FIGS. 1-6, the hand wheels 117 are rotated to secure the adapter 115 into the bottom portion 129 of the bracket opening 125 and, thereby, the ultrasonic transducers 120 against the outside surface of the conduit 101.

In view of the foregoing, the embodiments provide a simplified and effective assembly for allowing convenient installation and maintenance of ultrasonic transducers designed to be coupled to a conduit. A technical effect is a reduced amount and cost of hardware required for ultrasonic transducer maintenance.

This written description uses examples to disclose the embodiments, including the best mode, and also to enable any person skilled in the art to practice the embodiments, including making and using any devices or systems and performing any incorporated methods. The patentable scope of the embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for coupling an ultrasonic transducer to a conduit, the apparatus comprising:

an elongated housing configured to secure the ultrasonic transducer, the housing having a housing opening on the bottom thereof along a length of the housing, the housing opening configured to allow the ultrasonic transducer to transmit and receiving ultrasonic signals through the housing opening;

a base portion configured to be fastened to the conduit, the base portion comprising a bracket extending perpendicularly therefrom, the bracket comprising a bracket opening having an upper portion and a lower portion; and an adapter attached to the housing and configured to be placed into the bracket opening, wherein the adapter and the housing are not rotatable when the adapter is moved into the lower portion of the bracket opening, and wherein the adapter and the housing are rotatable when the adapter is moved into the upper portion of the bracket opening.

2. The apparatus of claim 1, further comprising at least one latch attached to the housing, the latch movable into an open position and a closed position, the closed position for securing the ultrasonic transducer against the conduit and the open position for rotating the housing and accessing the ultrasonic transducer.

3. The apparatus of claim 2, wherein the lower portion of the bracket opening includes a bracket edge that engages a side of the adapter when the adapter is moved into the lower portion for preventing rotation of the adapter and the attached housing, and wherein the upper portion of the bracket opening is circular and does not engage the side of the adapter when the adapter is moved into the upper portion.

4. The apparatus of claim 1, wherein the elongated housing comprises a longitudinal axis, and wherein the base portion is configured to be fastened to an outside surface of the conduit such that the longitudinal axis is substantially parallel to an axis of the conduit.

5. The apparatus of claim 1, further comprising a second base portion comprising a second bracket extending perpendicularly therefrom, the second bracket having a second bracket opening for receiving a second adapter placed therein, the second adapter attached to the housing.

6. The apparatus of claim 1, further comprising a spring inside the housing for pressing the ultrasonic transducer against the outside surface of the conduit.

7. The apparatus of claim 1, further comprising a spring inside the bracket for biasing the adapter and the housing attached thereto toward the outside surface of the conduit, thereby pressing the ultrasonic transducer against the conduit.

8. The apparatus of claim 1, wherein the housing comprises longitudinal rails adjacent the bottom opening upon which the ultrasonic transducer may be movably positioned.

9. The apparatus of claim 1, wherein the bottom opening of the housing comprises a narrow portion and a wide portion, and wherein the ultrasonic transducer may be movably positioned in the wide portion to remove the ultrasonic transducer from inside the housing.

10. The apparatus of claim 1, further comprising at least one hand wheel attached to at least one of the brackets, the hand wheel rotatable into an open position and a closed position, the closed position for securing the ultrasonic transducer against the conduit and the open position for rotating the housing and accessing the ultrasonic transducer.

11. The apparatus of claim 10, further comprising at least one strap having an adjustable length for fastening the base portion to the outside surface of the conduit, the strap for extending around the conduit along its outside surface.

12. The apparatus of claim 11, wherein the at least one strap further comprises visible measurement markings thereon for measuring a placement of additional fixtures on the conduit, and wherein the apparatus further comprises a spring washer positioned beneath the at least one strap.

13. The apparatus of claim 1, wherein the housing comprises an overhang that forms a gap between the overhang and an outside wall of the housing, the gap configured to receive a wire for electrically connecting to the ultrasonic transducer.

14. An apparatus for coupling an ultrasonic transducer to a conduit, the apparatus comprising:

base portions configured to be fastened to the conduit, the base portions each comprising a bracket extending perpendicularly therefrom, and each bracket comprising an opening having an upper portion and a lower portion;

a pair of adapters each configured to be placed into the opening of one of the brackets such that the adapters are not rotatable when moved into the lower portion of the opening, and are rotatable when moved into the upper portion of the opening;

an elongated housing having ends each attached to one of the adapters, the housing defining an inside of the housing and having an elongated bottom opening;

a pair of ultrasonic transducers secured inside the housing, the ultrasonic transducers for transmitting and receiving ultrasonic signals through the bottom opening of the housing; and at least one hand wheel attached to at least one of the brackets for biasing the housing toward the conduit while the adapters are positioned in the lower portions of the bracket openings, the at least one hand wheel for pressing the pair of ultrasonic transducers against the outside surface of the conduit.

15. The apparatus of claim 14, wherein the upper portion of the bracket openings are circular.

16. The apparatus of claim 15, wherein the lower portion of the bracket openings each include a bracket edge that engages a portion of the adapter for preventing rotation of the adapter and of the housing attached thereto.

17. The apparatus of claim 14, wherein the housing comprises a longitudinal axis, and wherein the base portions are configured to be fastened to an outside surface of the conduit such that the longitudinal axis is substantially parallel to an axis of the conduit.

18. The apparatus of claim 14, wherein each of the ultrasonic transducers is configured to be slidably moveable within the housing to positions operable for transmitting ultrasonic signals into the conduit and receiving echoes of the ultrasonic signals.

19. The apparatus of claim 14, further comprising straps for securing the base portions to the conduit.

20. The apparatus of claim 14, wherein the bottom opening of the housing comprises a narrow portion and a wide portion, and wherein either of the ultrasonic transducers may be moved into the wide portion to remove the either of the ultrasonic transducers from inside the housing.

* * * * *